United States Patent
Hashimoto et al.

[11] Patent Number: 6,069,701
[45] Date of Patent: May 30, 2000

[54] METHOD AND APPARATUS FOR MEASURING THE HEIGHT OF AN OBJECT

[75] Inventors: Yutaka Hashimoto, Atsugi; Hideaki Sasaki; Shinichi Kazui, both of Hadano, all of Japan

[73] Assignee: Hitachi, Ltd., Tokyo, Japan

[21] Appl. No.: 08/982,509

[22] Filed: Dec. 2, 1997

[30] Foreign Application Priority Data

Dec. 4, 1996 [JP] Japan ................................. 8-323797

[51] Int. Cl.[7] .......................... G01B 11/24; G01B 11/00; G01N 21/00
[52] U.S. Cl. .......................... 356/376; 356/375; 356/377; 356/359; 250/561
[58] Field of Search .................. 356/376, 375, 356/377, 359, 381; 250/561

[56] References Cited

U.S. PATENT DOCUMENTS

| | | | |
|---|---|---|---|
| 4,971,445 | 11/1990 | Sato et al. ........................ | 356/376 |
| 4,988,202 | 1/1991 | Nayar et al. . | |
| 5,023,916 | 6/1991 | Breu . | |
| 5,064,291 | 11/1991 | Reiser . | |
| 5,087,125 | 2/1992 | Narutaki ........................ | 356/375 |
| 5,355,221 | 10/1994 | Cohen et al. ........................ | 356/359 |
| 5,465,152 | 11/1995 | Bilodeau et al. . | |

FOREIGN PATENT DOCUMENTS 638801 2/1995 European Pat. Off. .
60-196608 10/1985 Japan .

*Primary Examiner*—Frank G. Font
*Assistant Examiner*—Roy M. Punnoose
*Attorney, Agent, or Firm*—Fay, Sharpe, Beall, Fagan, Minnich & McKee

[57] ABSTRACT

A method and an apparatus for measuring the height of an apex of an object with high accuracy without influence of the surface state of the object are disclosed. Correlation coefficients of respective positions of a waveform formed from digital data indicative of the height of the object detected by a head portion of a detector and a previously prepared standard waveform are calculated while moving the waveforms in the vertical and horizontal directions and the height of an apex position of the standard waveform at a position having a largest correlation coefficient from the calculated result is decided as the height of the apex of the object. Accordingly, the height of the apex can be decided from the whole detected waveforms without influence of local abnormality of the reflected light quantity waveform due to minute ruggedness or discoloration of the surface of the object.

16 Claims, 5 Drawing Sheets

METHOD AND APPARATUS FOR MEASURING THE HEIGHT OF AN OBJECT

BACKGROUND OF THE INVENTION

The present invention relates to a method and apparatus for measuring the height of the surface of an object. More particularly, the present invention relates to such a measuring method suitable for measurement of the height of a spherical object such as, for example, a solder bump formed on an electronic component such as a TAB (Tape Automated Bonding) and a semiconductor module such as an LSI, and furthermore the present invention relates to a measurement method of the height of an apex of a spherical object which is not positioned strictly and has a surface state which is not stabilized due to minute ruggedness or discoloration.

In the CCB bonding or the like, a large number of minute spherical solder bumps formed on an electronic component such as an LSI in the form of lattice are joined as electrodes. Accordingly, in order to ensure the reliability of connection, it is indispensable to inspect the height of all of the solder bumps before connection. Thus, it is necessary to measure the height of the apex of a spherical object at a high speed and with high accuracy.

Heretofore, there are known various methods of measuring the height of an object without contact therewith by means of the triangular surveying method using an optical beam. Of such methods, as a method of measuring the height of the apex of an object to be measured in case where the object is spherical and is not positioned strictly, that is, in case where the position of the apex of the object is not known exactly, there is a method in which X, Y and Z axes of the three-dimensional orthogonal coordinates are set and an optical beam is scanned relatively in the X-axis direction of the object as shown in FIG. 8A (801), so that a position of an inflection point on the scanned line is obtained from a quantity of reflected light of the optical beam by means of a method described later, the relative scanning operation of the optical beam being made in the Y-axis direction including the inflection point (802), so that a position of an inflection point on the scanned line is obtained from a quantity of reflected light similarly and this position is defined as a position 803 of the apex of the object as shown in FIG. 8B to thereby decide the height of this place to be the height of the object.

In the above decision method of obtaining the inflection point from the reflected light quantity, a center position between the position where the reflected light quantity exceeds a predetermined decision level and the position where the reflected light quantity is reduced to the decision level or less is decided as the inflection point.

A technique pertinent to the technique of this kind is described in JP-A-60-196608, for example.

SUMMARY OF THE INVENTION

The prior art described above does not consider the surface state of the object. More particularly, when discolored portion or rugged portion is formed in the surface of the object, reflection of light on the surface of the object is disturbed and accordingly a plurality of peaks of the reflected light quantity are produced. Hence, the position of the inflection point is decided wrongly and the height of the apex cannot be measured with high accuracy.

It is an object of the present invention to provide a method and an apparatus for measuring the height of an apex of an object with high accuracy without influence of the surface state of the object.

According to the present invention, a waveform formed from digital data indicative of the height of the object detected by a head portion of a detector and a previously prepared standard waveform are compared with each other while shifting the waveforms in the vertical and horizontal directions and correlation coefficients at shifted positions are calculated, so that the height of the apex of the object is calculated on the basis of a shift amount having a largest correlation coefficient of the calculated results and the height before shift of the standard waveform.

Accordingly, the height of the apex can be decided from the whole detected waveform without influence of local abnormality of the reflected light quantity waveform due to minute ruggedness or discoloration of the surface of the object.

In comparison of the waveforms, the widths of the waveforms to be compared are determined for each object on the basis of reflected light quantity data (digital data) of the objects.

Further, the standard waveform to be compared is prepared as follows: For example, when a plurality of spherical objects disposed on a base in the form of lattice like solder bumps disposed on an electronic component are measured, the standard waveform is formed from the height data of the plurality of objects obtained when the objects are scanned by one row in a predetermined direction and is updated for each scanning of row. Accordingly, even if a curvature, polish or the like of the surface of each object is varied due to change of a manufacturing lot, a manufacturing process or the like, the standard waveform can follow the change to thereby effect stable measurement.

Furthermore, in the measurement method, since the standard waveform data of reference is not previously set and is prepared for each scanning of row, an object of a kind having different height and diameter can be measured by the same method or apparatus.

DESCRIPTION OF THE PREFERRED EMBODIMENTS

An embodiment of the present invention is now described in detail with reference to the accompanying drawings.

Description is made to the case where a large number of solder bumps mounted on a base which is an electronic component or the like in the form of lattice are objects to be measured in the embodiment and the height of the apexes of the solder bumps is measured.

Figure 6:
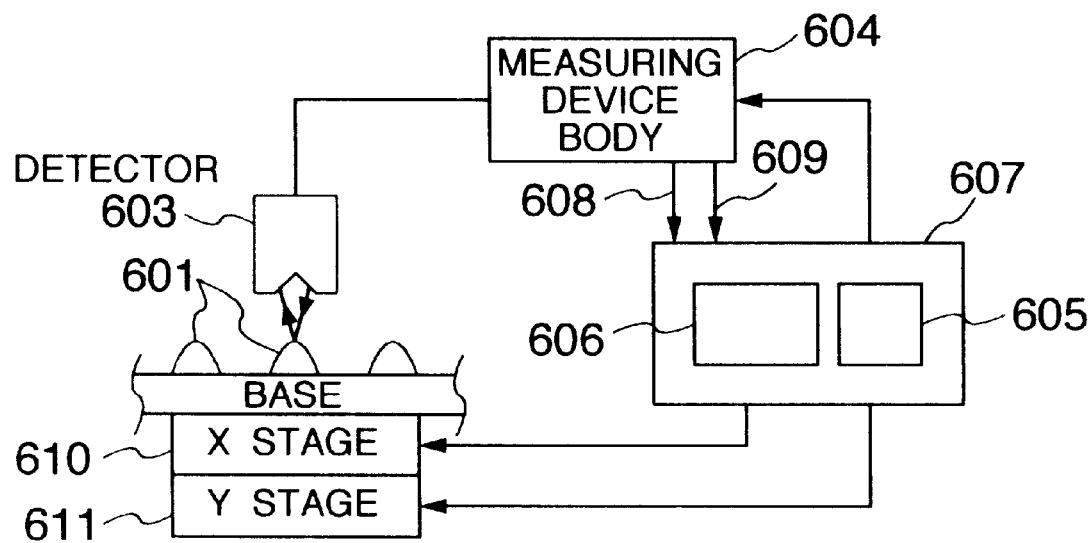
FIG. 6 is a diagram schematically illustrating a height measuring apparatus for performing the present invention.

FIG. 6 schematically illustrates a height measuring apparatus for performing the present invention.

A plurality of spherical bumps 601 to be measured are mounted on a base 602. Further, the bumps 601 are disposed in close vicinity to one another in the form of lattice.

In the embodiment, the bumps to be measured have a diameter of about 100 μm and a pitch of about 300 μm.

A detector 603 includes a detection head for measuring the height and including a light source for emitting an optical beam in the oblique direction and an element for detecting a position of reflected light. A distance of the bump 601 and the detector 603 is measured by the principle of the triangular surveying method and the height of the bump is detected on the basis of the measured value and a distance of the detector 603 and the base 602.

A reflected light quantity signal 608 and a height signal 609 detected by the detector 603 are sent from a measuring device body 604 to a controller 607 including a memory 605 and decision means 606. The base 602 is structured to be able to be moved in X and Y directions relatively to the detector 603 by moving an X stage 610 and a Y stage 611 in response to a command from the controller 607.

Figure 7:
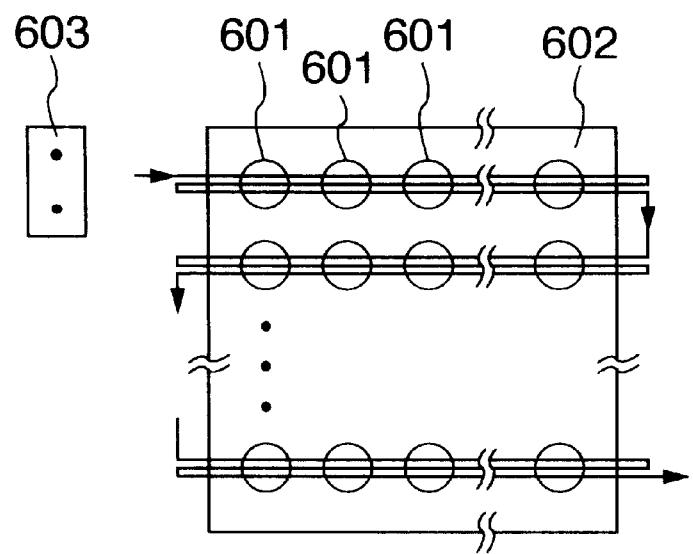
FIG. 7 is a diagram for explaining a scanning method of a stage.
Figure 8A:
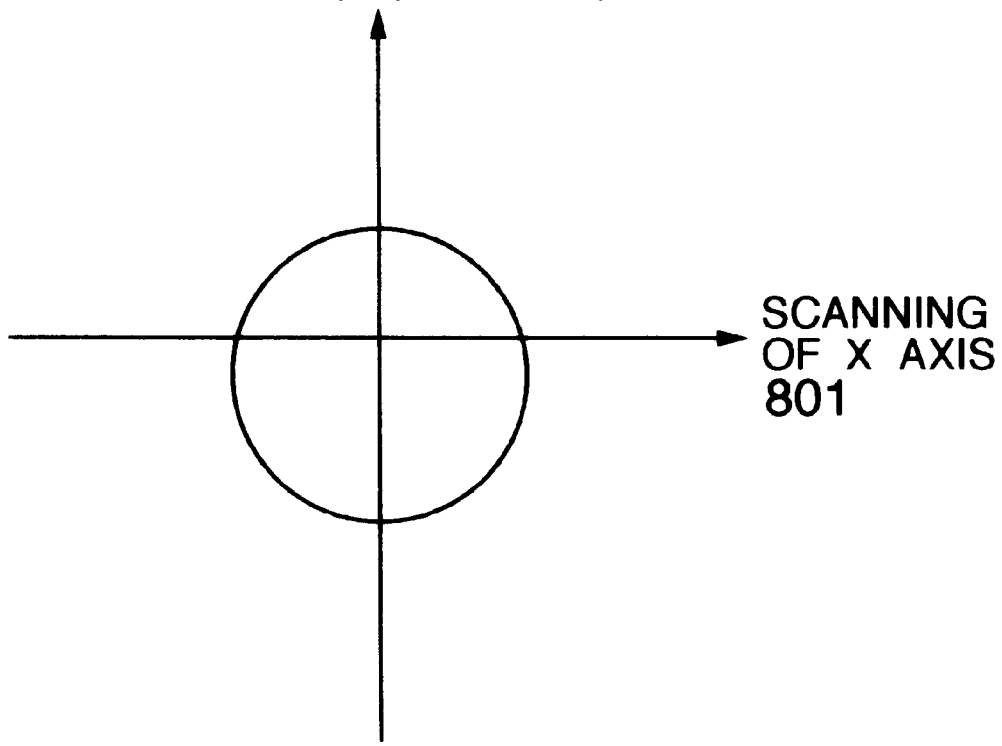
FIGS. 8A and 8B are diagrams illustrating a conventional measuring method.
Figure 8B:
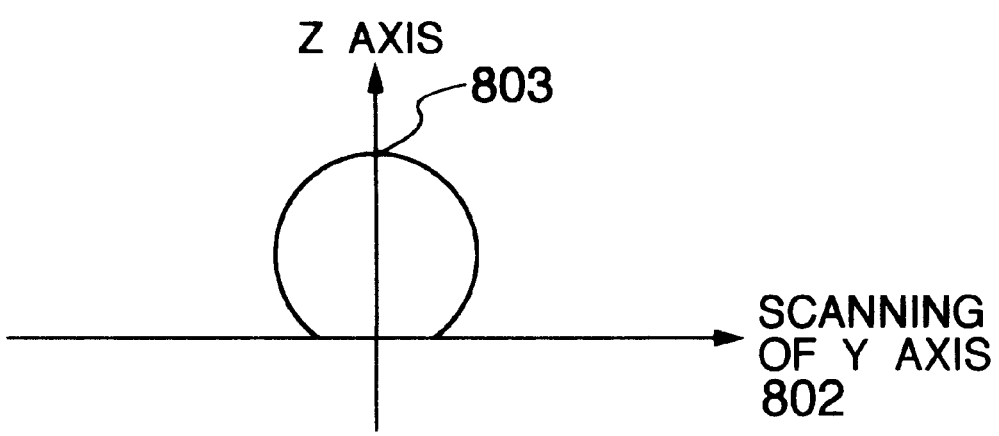

FIG. 7 shows the relative scanning method of the detector 603 to the bumps 601 to be measured.

The detector 603 scans the vicinity of the apexes of the bumps 601 on the base 602 by plural times for each row in the X direction and samples the reflected light quantity signals 608 and the height signals 609 for one row, which are stored in the controller 607. This scanning operation is repeated while shifting the Y stage 611 for each row of bumps to scan all of the bumps 601 on the base 602.

Figure 1:
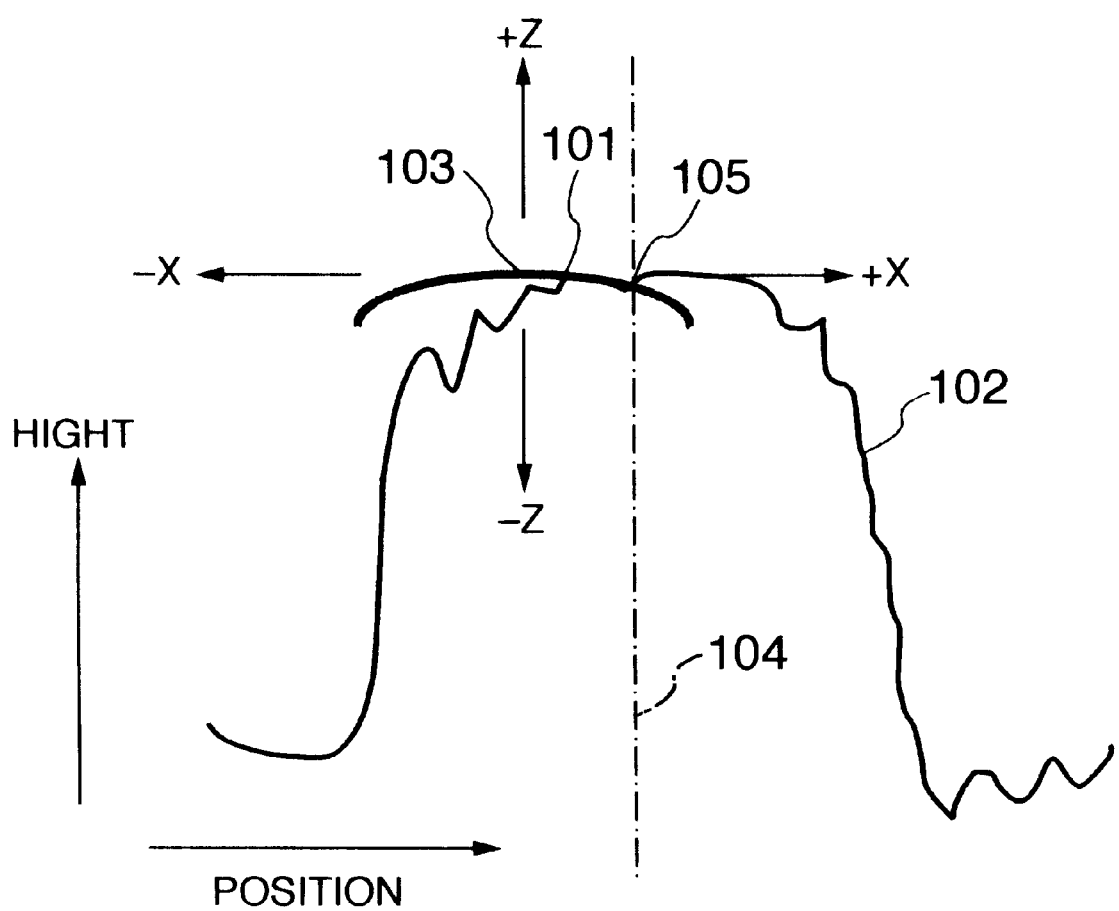
FIG. 1 is a diagram schematically illustrating a principle of the waveform matching of the present invention.

FIG. 1 is a diagram for explaining the principle of deciding the apex in the embodiment.

A variation waveform 102 corresponds to a height signal of one bump 601. A standard waveform 101 is a standard model waveform in the vicinity of the apex of the bump prepared by a method described later. A provisional center position 104 of the variation waveform 102 represents a provisional center position calculated on the basis of a design position in case where the bump is scanned and the height information and the reflected light quantity information by means of a conventional method.

First, a position 103 of an apex of the standard waveform and a position 105 of a provisional apex of the variation waveform 102 are superposed on each other to calculate a correlation coefficient. The apex position 103 of the standard waveform at the time when the center axis of the standard waveform is aligned with the center axis of the variation waveform is set as the origin and X and Y axes are defined in the scanning direction of the detector and in the height direction, respectively. The correlation coefficient is calculated from values of the X coordinates of the standard waveform and the variation waveform which are gatherings of data points and values of the Z coordinates at the X coordinates and the calculated result is stored in the memory 605 of the controller 607.

Incidentally, the correlation coefficient represents the coincidence degree in shape of the variation waveform 102 and the standard waveform 101 quantitatively and the larger correlation coefficient represents that the shapes of two waveforms are more similar to each other.

In the embodiment, a width in the X coordinates is set to 2 μm, although the width can be set to any value in accordance with a size of a bump and accuracy.

Furthermore, the standard waveform 101 is shifted in the X or Z direction. Actually, a cut position in the range of comparison of the variation waveform 102 is shifted in the vertical direction or the horizontal direction, so that the correlation coefficient is calculated similarly. The comparison and calculation in each shift in the vertical and horizontal direction are repeatedly effected within a predetermined range and the correlation coefficients in the respective cases are calculated. A sum of a shift amount in the Z direction from the origin of a position having the largest correlation coefficient of the calculated values and the height of the position 103 of the apex of the standard waveform 101 is decided as the height of the apex of the bump on the scanning line.

The shift range in the Z direction is previously determined in accordance with the accuracy of an apparatus for forming solder bumps. For example, the shift range is set to be about one and a half times of a difference of a lowest solder bump and a highest solder bump capable of being manufactured by a solder bump forming apparatus. Further, the shift pitch is set to about the resolution of measurement of the detector 603.

Figure 4:
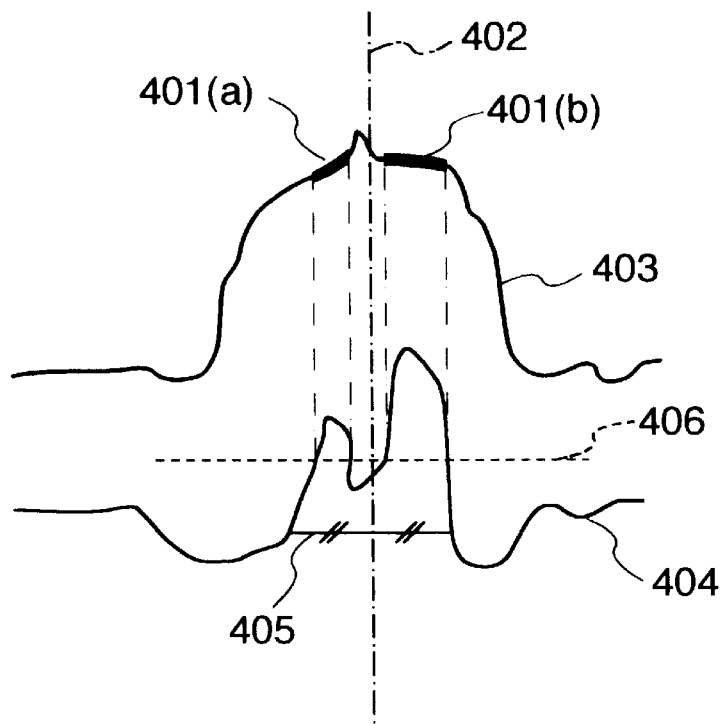
FIG. 4 is a diagram for explaining a calculation principle of effective data which is original data of a standard waveform with respect to one bump of the scanned bumps by one row.

In the embodiment, as shown in FIG. 7, since the scanning operation is repeatedly made three times for the solder bumps of one row, three apex height values are obtained for one bump, while an apex height value having a largest width of a light quantity waveform exceeding a threshold level of the reflected light quantity shown in FIG. 4 is adopted as a true apex height.

Figure 2:
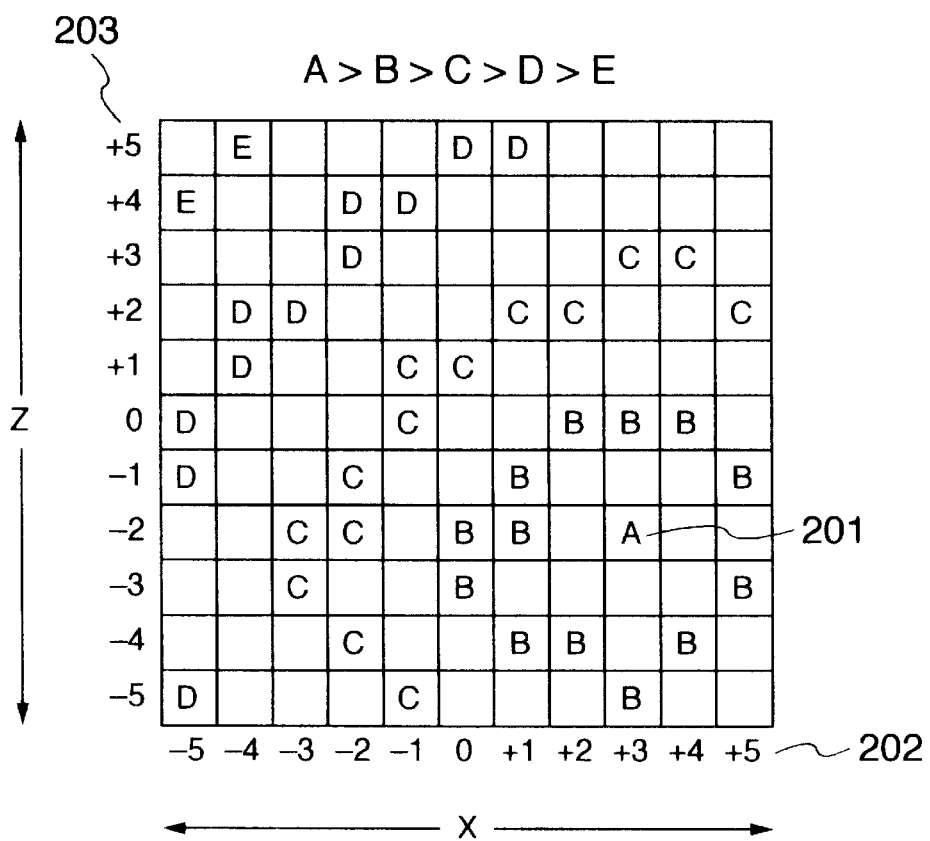
FIG. 2 shows contour lines expressing the distribution of correlation coefficients in each shift.

FIG. 2 shows an example representing the relation of the correlation coefficients calculated by effecting shift by ±5 times in the X and Z directions by means of the above method and the positions thereof.

In FIG. 2, portions designated by A, B, C, D and E (A>B>C>D>E) represent points indicative of the correlation coefficients which are substantially identical for each letter and are expressed by X and Y shift amounts. Thus, the correlation coefficients are distributed into concentric circles about the position of A (201) having the largest correlation coefficient.

Accordingly, there is also a method in which calculation is made for only some points in case of a bump the provisional apex position 105 of which is not known, for example, and the scanning operation is made about the vicinity of the point indicating a largest correlation coefficient thereof to effect calculation. Further, there is also a method in which comparison and calculation means for simply counting differences in the Z coordinates of the variation waveform and the standard waveform instead of the correlation coefficient is used to judge that the point having a smallest total value of differences is a place in which the variation waveform and the standard waveform are most coincident with each other. In addition, a method in which the reflected light quantities at respective places are examined in the range of the variation waveform 102 to be compared so that the height signals of positions which do not reach a previously set reference value are not subjected to the comparison and calculation can prevent reduction of the decision accuracy due to wrong signals. Such various methods can be selected freely in accordance with the sampling speed of the detector, the speed of the decision and calculation device, a necessary measurement accuracy, a size of a work to be measured or the like.

Figure 5:
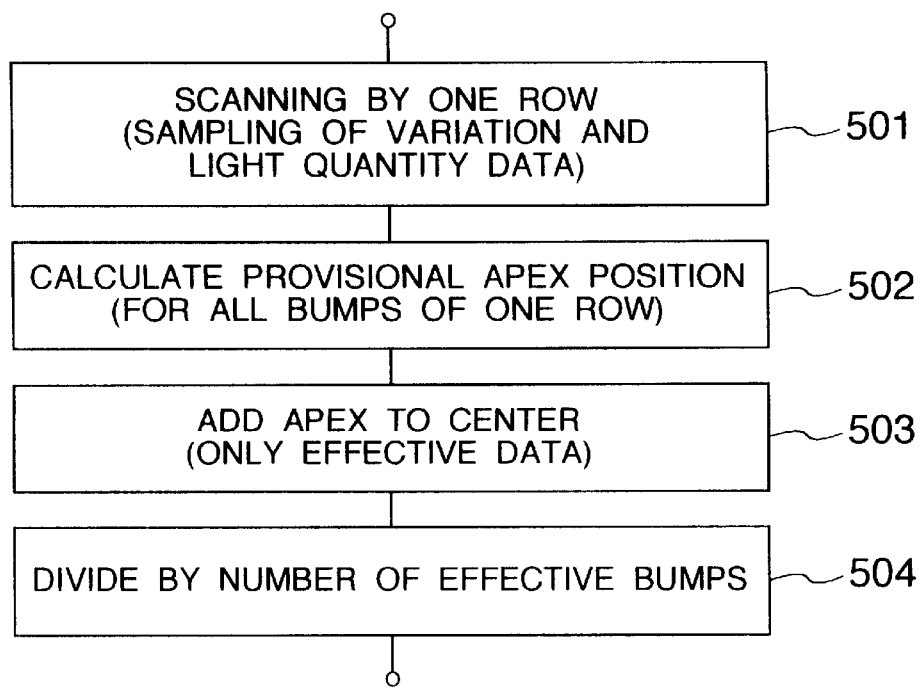
FIG. 5 is a flow chart showing a procedure of preparing a standard waveform.

A method of preparing the standard waveform 101 is now described with reference to FIGS. 3, 4 and 5.

Figure 3:
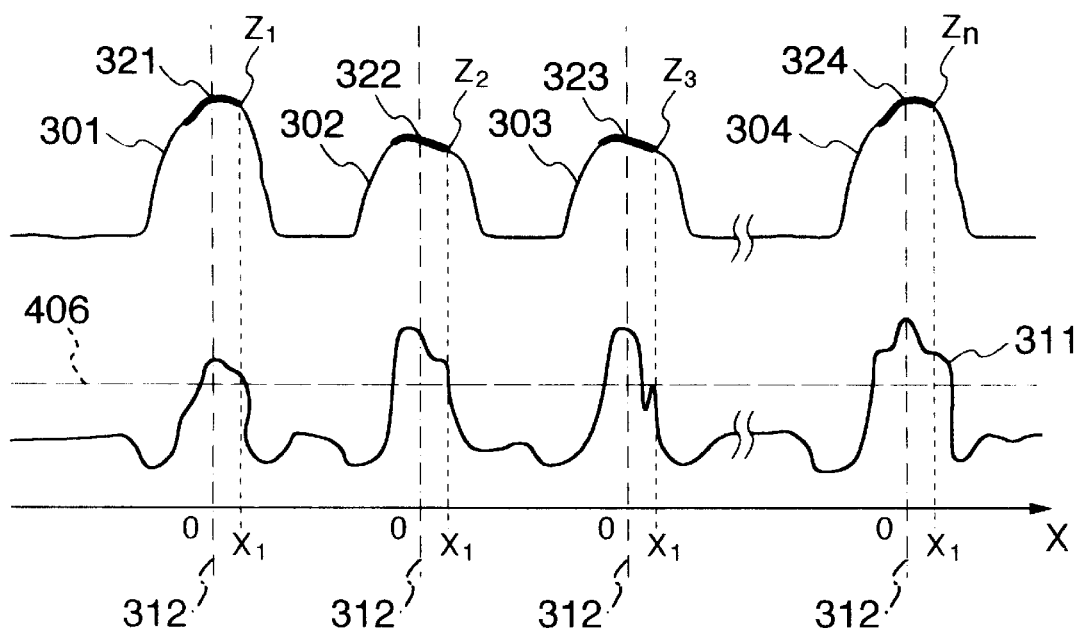
FIG. 3 is a diagram showing variation and light quantity obtained when bumps of one row are scanned.

FIG. 3 is a diagram showing variation waveforms 301, 302, 303 and 304 and a light quantity waveform 311 of bumps obtained by scanning bumps of one row (n bumps). FIG. 4 is an enlarged view of a waveform of a bump. FIG. 5 is a flow chart showing a procedure of preparing the standard waveform.

The fundamental principle for preparing the standard waveform which is a model used upon comparison and decision is to average waveforms of bumps to be compared and decided.

Incidentally, the effective data used when the standard waveform is obtained is described.

In FIG. 4, numeral 403 represents a detected variation waveform and 404 a waveform of a reflected light quantity. Only the reflected light quantities expressed by the waveform 404 and exceeding a second threshold level 406 for decision of the effective data are used as the effective data of variation used when the standard waveform is obtained and variation data smaller than the second threshold level 406 is not used. That is, in FIG. 4, portions 401(*a*) and 401(*b*) of the variation waveform 403 are adopted as the effective data for preparing the standard waveform since the reflected light quantities thereof exceed the second threshold level 406, while variation data of other portions is not adopted as the effective data for preparing the standard waveform.

The procedure of preparing the standard waveform is now described.

First, variation and reflected light quantities of bumps for each row are detected to extract variation waveforms and light quantity waveforms (501). For example, the variation waveforms and light quantity waveforms for the bumps represented by 301, 302, 303 and 304 of FIG. 3 are extracted. In FIG. 3, only four bumps for one row are shown, while actually several tens to several hundreds bumps are provided.

Next, a position of a provisional apex of each waveform is obtained (502). In FIG. 4, a provisional center position 402 is obtained as a center position for a width of a waveform existing until the reflected light quantity is lower than a first threshold level 405 for decision of the center position after the reflected light quantity exceeds the first threshold level 405 and an intersection of the center position and the variation waveform is defined as a provisional apex position.

In the embodiment, two threshold levels for decision of the effective data and decision of the center position are used as threshold levels of the reflected light quantity. It is desirable that effective data having as large the reflected light quantity as possible is used to improve the accuracy, while when such a high level threshold is used to obtain the center position, there is the possibility that an exact center position cannot be decided since the center position is obtained for each peak when two or more peaks of reflected light quantity can be produced due to the surface state of a bump. Accordingly, a lower level threshold is used to decide the center position so that only one center position is obtained for each bump. However, the threshold level can be set to an intermediate value which has the function of both threshold levels for decision of the effective data and the center position.

The second threshold level is used to extract effective data from the extracted waveform and the effective data 321, 322, 323 and 324 are added and averaged for all bumps of the scanned row (503, 504). The addition and average method is made as follows: The X axis (the provisional center position is the origin O) is set in the scanning direction and the Z axis (the base plane is the origin O) is set in the height direction. Values of the Z coordinates of the effective data for each of the X coordinates are added for all bumps (503) and the sum thereof is divided by the number of the added coordinates (504). For example, when the Z coordinates ($Z_1 \ldots Z_n$) for a specific X-coordinate $X_1$ are effective data in 80 bumps of 100 bumps in a row, respective values of 80 Z-coordinates are added and the sum thereof is divided by 80. In FIG. 3, since only $Z_1$, $Z_2$ and $Z_n$ are effective data and $Z_3$ is not effective data, values of $Z_1$, $Z_2$ and $Z_n$ are added and the sum thereof is divided by 3.

As described above, the gathering of the added and averaged values of the Z coordinates of the effective data in the X coordinates constitutes the standard waveform.

When the standard waveform is prepared, the above-described comparison operation is effected immediately so that the correlation coefficient is calculated while shifting the detected variation waveform and standard waveform. When the comparison operation at the scanning row is completed, the stored standard waveform data is cleared and the scanning operation is made for a next row, so that the preparation of the standard waveform and the comparison operation are performed for the next row. This processing operation is repeated for all of the bump rows.

In FIG. 4, the effective data are divided into two portions, while the averaging processing of the effective data is performed for each point of all of the bumps for one row and accordingly the division of the effective data is not a problem. Further, even if the finally prepared standard waveform is divided, the standard waveform is treated as the gathering of points upon comparison and calculation and accordingly the division of the standard waveform is not an obstacle.

Further, the standard waveform for comparison is prepared from the height data of a plurality of bumps obtained when the solder bumps of one row are scanned and is updated for each scanning of the row and accordingly even if a curvature, polish or the like of the bump surface is varied due to change of a manufacturing lot, a manufacturing process or the like, the standard waveform can follow the change to thereby effect stable measurement. Furthermore, in this measurement method, the standard waveform data for reference is not set previously and is prepared for each scanning of the row. Accordingly, bumps of another kind having different height and diameter can be measured by the same method or apparatus.

As described above, according to the present invention, since the method of comparing the standard waveform and the variation waveform in the vicinity of the apex is used to decide the height of the apex of the object such as, for example, the spherical object such as solder bumps instead of using a waveform of the reflected light quantity, the decision does not have no relation to disturbance of the waveform of the reflected light quantity and is not influenced by ruggedness of the surface of the object. Further, since the standard waveform is not required to have the absolute reference and is prepared from the object itself to be measured at real time, the standard waveform can cope with change of a kind of the object or the like with flexibility.

What is claimed is:

1. A method of measuring the height of an object, comprising the steps of:

extracting data indicative of the height of the surface of the object by utilization of light;

changing relative positions of a previously provided standard waveform with respect to a waveform obtained from said height data arbitrarily;

calculating correlation coefficients of said waveform and said standard waveform at each of said changed positions; and deciding the height of an apex of the object from said calculated result.

2. A method according to claim 1, wherein said step of extracting the data of the height, comprises:

irradiating light to the object;

detecting positions of the light reflected by the surface of the object; and detecting the height of the surface of the object from said detected positions.

3. A method according to claim 1, wherein said step of changing the positions, comprises:

superposing a center position of said waveform onto a center position of said standard waveform;

moving said waveform or said standard waveform by any distance in any direction from said superposed position; and repeating the operation of moving said waveform or said standard waveform by any distance in any direction from said moved position by any number of times.

4. A method according to claim 1, comprising:

superposing a center position of said waveform onto a center position of said standard waveform; and moving said standard waveform from said superposed position in a vertical or horizontal direction by a predetermined distance and repeating the operation of moving said standard waveform by the predetermined distance in the vertical or horizontal direction from said moved position by any number of times.

5. A method according to claim 1, wherein said step of deciding the height, comprises:

deciding the height of an apex position of said standard waveform at a position having a largest value of said correlation coefficients at the positions as the height of the apex of the object.

6. A method according to claim 3, wherein said step of deciding the height, comprises:

deciding the height of an apex position of said waveform or said standard waveform at a position having a largest value of said correlation coefficients at the positions as the height of the apex of the object.

7. A method according to claim 4, wherein said step of deciding the height, comprises:

deciding an added result of a movement amount in a vertical direction to a position having a largest value of the correlation coefficients of said positions and the height of the apex position of said standard waveform as the height of the apex of said object.

8. A method of measuring the height of a plurality of objects mounted on an upper surface of a base in a row, comprising the steps of:

irradiating light to the objects disposed in each row;

scanning each row by light;

detecting positions of light reflected by surfaces of the objects in each row to thereby extract data indicative of the height of the surfaces of the objects;

changing a relative position of a previously prepared standard waveform with respect to waveforms corresponding to the objects obtained from said height data for each of said waveforms arbitrarily;

calculating correlation coefficients of said waveform and said standard waveform in said changed positions; and deciding the height of apexes of the objects for each row from said calculated result.

9. A method according to claim 8, wherein said step of changing said position, comprises:

superposing a center position of said waveform onto a center position of said standard waveform;

moving said waveform or said standard waveform from said superposed position in any direction by any distance; and repeating the operation of moving said waveform or said standard waveform from the moved position in any direction by any distance by any number of times.

10. A method according to claim 8, comprising:

superposing a center position of said waveform onto a center position of said standard waveform; and moving said standard waveform from said superposed position in a vertical or horizontal direction by a predetermined distance and repeating the operation of moving said standard waveform by the predetermined distance in the vertical or horizontal direction from said moved position by any number of times.

11. A method according to claim 8, wherein said step of deciding the height, comprises:

deciding the height of an apex position of said standard waveform at a position having a largest value of said correlation coefficients at the positions as the height of the apex of the object.

12. A method according to claim 9, wherein said step of deciding the height, comprises:

deciding the height of an apex position of said waveform or said standard waveform at a position having a largest value of said correlation coefficients at the positions as the height of the apex of the object.

13. A method according to claim 10, wherein said step of deciding the height, comprises:

deciding an added result of a movement amount in a vertical direction to a position having a largest value of the correlation coefficients of said positions and the height of the apex position of said standard waveform as the height of the apex of said object.

14. A method according to claim 8, wherein said standard waveform is prepared for each row by:

scanning the objects disposed in each row by light;

detecting positions of light reflected by surfaces of the objects in each row and reflected light quantities to thereby extract data indicative of the height of the surfaces of the objects and light quantity data;

extracting data corresponding to the light quantity data exceeding a predetermined level, of the height data of the surfaces of the objects as effective data; and adding and averaging the effective data for each row.

15. An apparatus for measuring the height of an object, comprising:

a stage capable of being moved in front and rear directions and in right and left directions;

detection means for irradiating light to the object mounted on said stage and detecting positions of light reflected by a surface of the object;

measurement means for extracting data indicative of the height of the surface of the object from the positions of the reflected light detected by said detection means;

memory means for storing said extracted height data and a previously provided standard waveform; and decision means for changing a relative position of said standard waveform to a waveform obtained from said height data arbitrarily and calculating correlation coefficients of said waveform and said standard waveform in said changed positions to decide the height of an apex of the object from said calculated result.

16. An apparatus according to claim 15, wherein said decision means includes:

means for deciding the height of an apex position of said standard waveform at a position having a largest value of said correlation coefficients of said positions as the height of the apex of the object.

* * * * *